US010500282B2

(12) United States Patent
Desai et al.

(10) Patent No.: US 10,500,282 B2
(45) Date of Patent: Dec. 10, 2019

(54) SUPERSATURATED STABILIZED NANOPARTICLES FOR POORLY SOLUBLE DRUGS

(71) Applicant: Kashiv BioSciences, LLC, Bridgewater, NJ (US)

(72) Inventors: Dipen Desai, Whippany, NJ (US); Wantanee Phuapradit, Montville, NJ (US); Anekant Jain, North Brunswick, NJ (US); Atsawin Thongsukmak, Piscataway, NJ (US); Navnit H. Shah, Clifton, NJ (US)

(73) Assignee: Kashiv BioSciences, LLC, Bridgewater, NJ (US)

( * ) Notice: Subject to any disclaimer, the term of this patent is extended or adjusted under 35 U.S.C. 154(b) by 27 days.

(21) Appl. No.: 14/653,061

(22) PCT Filed: Dec. 19, 2013

(86) PCT No.: PCT/US2013/076534
§ 371 (c)(1),
(2) Date: Jun. 17, 2015

(87) PCT Pub. No.: WO2014/100403
PCT Pub. Date: Jun. 26, 2014

(65) Prior Publication Data
US 2015/0335753 A1 Nov. 26, 2015

Related U.S. Application Data

(60) Provisional application No. 61/739,472, filed on Dec. 19, 2012.

(51) Int. Cl.
| | |
|---|---|
| *A61K 47/32* | (2006.01) |
| *A61K 31/57* | (2006.01) |
| *A61K 31/421* | (2006.01) |
| *A61K 31/58* | (2006.01) |
| *A61K 38/08* | (2019.01) |
| *A61K 31/496* | (2006.01) |
| *A61K 38/07* | (2006.01) |
| *A61K 31/5377* | (2006.01) |
| *A61K 9/16* | (2006.01) |

(52) U.S. Cl.
CPC ............ *A61K 47/32* (2013.01); *A61K 31/421* (2013.01); *A61K 31/496* (2013.01); *A61K 31/5377* (2013.01); *A61K 31/57* (2013.01); *A61K 31/58* (2013.01); *A61K 38/07* (2013.01); *A61K 38/08* (2013.01); *A61K 2800/5424* (2013.01); *A61K 2800/5426* (2013.01)

(58) Field of Classification Search
CPC ...... A61K 47/32; A61K 31/57; A61K 31/421; A61K 31/58; A61K 38/08; A61K 31/496; A61K 38/07; A61K 31/5377; A61K 2800/5426; A61K 9/1635; A61K 9/1676; A61K 9/10
See application file for complete search history.

(56) References Cited

U.S. PATENT DOCUMENTS

| | | | |
|---|---|---|---|
| 4,196,188 A | 4/1980 | Besins | |
| 4,927,816 A | 5/1990 | Ester | |
| 5,422,376 A * | 6/1995 | Webb | A61K 9/0048 514/781 |
| 6,153,225 A * | 11/2000 | Lee | A61K 9/146 264/4.1 |
| 6,248,363 B1 | 6/2001 | Patel et al. | |
| 6,649,659 B1 | 11/2003 | Dearn | |
| 7,771,755 B2 * | 8/2010 | Li | A61K 38/1875 424/499 |
| 2004/0131553 A1 | 7/2004 | Besse | |
| 2004/0266890 A1 * | 12/2004 | Kipp | A61K 9/10 516/20 |
| 2005/0063913 A1 | 3/2005 | Pruitt et al. | |
| 2005/0119226 A1 * | 6/2005 | Walter | C07F 5/025 514/64 |
| 2006/0198896 A1 * | 9/2006 | Liversidge | A61K 9/0019 424/489 |
| 2008/0227805 A1 * | 9/2008 | Luangdilok | A61K 9/0019 514/282 |

(Continued)

FOREIGN PATENT DOCUMENTS

| | | |
|---|---|---|
| CN | 102451469 A | 5/2012 |
| WO | 200000179 A1 | 1/2000 |
| WO | 2008065506 A2 | 6/2008 |
| WO | WO 2012101242 A1 * | 8/2012 ........... A61K 9/0024 |

OTHER PUBLICATIONS

Indrajit Ghosh et al: "Nanosuspension for improving the bioavailability of a poorly soluble drug and screening of stabilizing agents to inhibit crystal growth", International Journal of Pharmaceutics, vol. 409, No. 1-2, May 1, 2011 (May 1, 2011 ), pp. 260-268, XP055112634, ISSN: 0378-5173, DOI:10.1016/j.ijpharm.2011.02.051.

(Continued)

*Primary Examiner* — Trevor Love
(74) *Attorney, Agent, or Firm* — Lerner, David, Littenberg, Krumholz & Mentlik, LLP

(57) ABSTRACT

A pharmaceutical composition and method of producing supersaturated stabilized nanoparticles of poorly soluble drugs having average sizes less than 1 μm, or less than 800 nm, or less than 500 nm, comprising at least one pharmaceutically active ingredient, a hydrophilic polymer, a water-soluble surfactant, and subsequently stabilized by ionic polymers.

9 Claims, No Drawings

(56) References Cited

U.S. PATENT DOCUMENTS

2010/0062073 A1* 3/2010 Beyerinck ............ A61K 9/5161
424/491
2012/0142649 A1* 6/2012 Gray .................... A61K 9/0024
514/171

OTHER PUBLICATIONS

International Search Report & Written Opinion for Application No. PCT/US2013/076534 dated May 6, 2014.
J. Brouwers et al., "Supersaturating Drug Delivery Systems: The Answer to Solubility-Limited Oral Bioavailability?", Journal of Pharmaceutical Sciences, vol. 9(8), pp. 2549-2572, 2009.

Navnit Shah et al: "Development of novel microprecipitated bulk powder (MBP) technology for manufacturing stable amorphous formulations of poorly soluble drugs", International Journal of Pharmaceutics, val. 438, No. 1-2, November 2812 (2812-11), pp. 53-68, XP855112582, ISSN: 8378-5173, DOI:18.1816fj.ijpharm. 2812.88.831 the whole document p. 59-p. 68.
Sarita Kumari Yadav et al: "Eudragit-Based Nanosuspension of Poorly Water-Soluble Drug: Formulation and-Evalua", AAAPS PHARMSCITECH, Springer New York LLC, US, vol. 13, No. 4, Aug. 15, 2012 (Aug. 15, 2012), pp. 1031-1044, XP035148003, ISSN: 1530-9932, DOI: 1 0.1208/S12249-012-9833-0.
Wei Sun et al: "Effect of novel stabilizers-cationic polymers on the particle size and physical stability of poorly soluble drug nanocrystals", Nanomedicine: Nanotechnology, Biology and Medicine, val. 8, No. 4, May 1, 2012 (May 1, 2012), pp. 460-467, XP055112931, ISSN: 1549-9634, DOI: 10.1016/j.nano.2011.07.006.

* cited by examiner

SUPERSATURATED STABILIZED NANOPARTICLES FOR POORLY SOLUBLE DRUGS

CROSS-REFERENCE TO RELATED APPLICATIONS

The present application is a national phase entry under 35 U.S.C. § 371 of International Application No. PCT/US2013/076534, filed Dec. 19, 2013, published in English, which claims priority from U.S. Provisional Application No. 61/739,472, filed Dec. 19, 2012, all of which are incorporated herein by reference.

BACKGROUND

Aspects of the present application relate to pharmaceutical dosage forms containing particulate active ingredients that have limited water solubility. In embodiments, the dosage forms are intended to be administered orally to provide systemic absorption of an active ingredient from the gastrointestinal tract.

Much effort has been directed to improving the bioavailability and other pharmacological properties of drug substances. The needs are particularly acute for orally administered solid dosage forms of active ingredients that have limited solubility in water, since the gastrointestinal tract is a generally aqueous environment and many factors influence the ability of drug particles to become available for systemic absorption.

In general, it has been accepted that using smaller particles of an active pharmaceutical ingredient will enhance its oral bioavailability; rate of solubilization for particulate substances tend to increase as the particle sizes decrease, due to an increased particle surface area. However, using smaller particles in pharmaceutical dosage form production causes complications, since the smaller particles are not as easily handled. Flowability of particles frequently is lessened as their sizes decrease. Blending small particles with larger particles frequently results in poor uniformity of the blend. Also, various factors, including the surface electrical charges that can be present on small particles, promote undesired and unpredictable phenomena, such as agglomeration, that result in effectively increasing the original particle sizes during the handling and processing of powders.

U.S. Pat. No. 4,196,188 discloses difficulties encountered with the oral administration of progesterone in solid dosage forms. It is reported that compression of powders having small particle sizes results in modification of the granulometric distribution of the starting particles. The problems were overcome by providing a suspension of progesterone particles, at least 80% having sizes of 5-15 μm, in an oil vehicle that is filled into capsules. Such particle sizes were obtained by mixing recrystallized progesterone with arachid oil and milling the mixture in a cooled rotor mill that maintained temperatures of 25-30° C. Micronized progesterone is described as being very hygroscopic and electrostatic when the particles sizes are less than 20 μm, and exhibits particle size increases during storage that decrease drug bioavailability. This patent is believed to relate to the commercial product PROMETRIUM® progesterone capsules. However, use of the disclosed oil is presently not favored in pharmaceutical products, due to the prevalence of allergic reactions.

U.S. Pat. No. 4,927,816 discloses a sublingual capsule formulation comprising particles of progesterone having sizes less than 5 μm, in combination with a salivation stimulator.

U.S. Patent Application Publication No. 2004/0131553 discloses tablets containing a progestin, prepared by a procedure including co-micronizing the drug with a surfactant, preferably an ionic surfactant such as sodium lauryl sulfate. The co-micronization could involve dry ingredients, using a jet mill, or could be solid/liquid co-micronization, using a colloid mill or ball mill. According to this publication, micronizing the drug is not an automatic means for increasing bioavailability, as additional formulation development steps can be required; the effects of particle size reduction on solubility and bioavailability were said to be unpredictable.

U.S. Pat. No. 6,649,659 discloses the preparation of atovaquone suspensions, by passing an aqueous mixture containing 2.5 w/v atovaquone and 0.25% w/v Celacol™ M2500 (methyl cellulose) through a MICROFLUIDIZER™, producing suspensions having a mean drug particle size of 1 μm. The suspension had a higher drug bioavailability than another suspension having 3 μm mean size drug particles.

U.S. Pat. No. 6,248,363 discloses improving the dissolution and/or absorption of a number of drug substances, by coating a solution of a drug and a hydrophilic surfactant, or a mixture of hydrophilic and lipophilic surfactants, onto solid carrier particles. An example describes coating nonpareil seeds with a mixture of progesterone, a PEG-24 cholesterol ether (hydrophilic surfactant), and the lipophilic components distilled monoglycerides and deoxycholic acid.

U.S. Patent Application Publication No. 2005/0063913 discloses wet milling of metaxalone in the presence of povidone and docusate sodium, to prepare dispersions of nanoparticles of the drug.

The use of drug solutions for making solid dosage forms is not preferred, since the exact physical form of the drug in the finished dosage unit is not necessarily known or predictable. Also it is difficult to make soluble dosage form with acceptable size for oral administration due to poor solubility of drug in polymeric carriers or oils. A need remains for pharmaceutical dosage forms that contain low-solubility drug substances and have reproducible desired bioavailability characteristics.

There is a need to develop formulations having at least one of the following features:

i) Drugs can be produced as nanosuspensions with the smallest particle sizes in the range of 50 to 800 nm.

ii) Nanoparticles can maintain their primary particle sizes after downstream processing into solid pharmaceutical dosage forms.

iii) Drugs maintain supersaturation solubility profiles or superior dissolution characteristics, compared to their conventional oral dosage forms.

SUMMARY OF THE INVENTION

In one aspect, the present application provides a suspension comprising water, drug particles having average sizes less than 1 μm, a water-soluble surfactant, and a water-soluble polymer, where the drug particles have been subjected to particle size reduction using a fixed-geometry fluid processor.

In a further aspect, the application provides a suspension comprising: water; a drug selected from the group consisting of abiraterone, boceprivir, metaxalone, progesterone, telaprevir, and ziprasidone, or their pharmaceutically acceptable salts, esters, or solvates, in the form of particles having average sizes less than 1 µm; a water-soluble surfactant; and a water-soluble polymer. In embodiments, average drug particle sizes in a suspension are less than 800 nm, or less than 500 nm.

Suspensions of the application can be used to make solid pharmaceutical dosage forms. Embodiments of the dosage forms include capsules having pharmacologically inert particulate supports that are coated with a drug-containing suspension and dried, and optionally further coated with a coating polymer. Other embodiments include tablets compressed from blends of pharmaceutical excipients and pharmacologically inert particulate supports that are coated with a drug-containing suspension and dried.

In another aspect of the invention is a stabilized nano-suspension comprising an aqueous solution comprising a water-soluble surfactant and a water-soluble polymer, wherein particles of a pharmaceutically active ingredient are suspended within said aqueous solution and combining a de-agglomeration agent with said aqueous solution, wherein said de-agglomeration agent maintains an average size of said particles of less than about 800 nm; and wherein said de-agglomeration agent maintains a supersaturated concentration of said pharmaceutically active ingredient above a solubility of said pharmaceutically active ingredient in said nanosuspension.

In a further embodiment of the invention the de-agglomeration agent is an anionic polymer. In still a further embodiment of the invention the anionic polymer is a copolymer of methacrylic acid and an acrylate selected from the group consisting of ethyl acrylate, methacrylate, and methyl methacrylate. In another embodiment of the invention the de-agglomeration agent is a cationic polymer. In still another embodiment of the invention the cationic polymer is based on a copolymer of dimethylaminoethyl methacrylate, butyl methacrylate, and methyl methacrylate.

In another embodiment of the invention the ratio of the pharmaceutically active ingredient to the de-agglomeration agent is between 20:1 to 1:20. In a further embodiment the ratio of the pharmaceutically active ingredient to the de-agglomeration agent is between 5:1 to 1:5. In another embodiment of the invention the ratio of the pharmaceutically active ingredient to the de-agglomeration agent is between 3:1 to 1:3.

Some embodiments of the invention provide for a pharmaceutical composition comprising particles of a poorly soluble drug having average sizes less than about 1 µm, or less than about 800 nm, or less than about 500 nm, the particles being prepared by a size reduction procedure with an aqueous medium containing suspended drug, a water-soluble surfactant, and a water-soluble polymer.

In other embodiments, the pharmaceutical composition comprises a pharmaceutically agent comprising any one or more of abiraterone, acutretin, albendazole, albuterol, aminogluthemide, amiodarone, amlodipine, amphetamine, amphotericin B, atorvastatin, atovaquone, azithromycin, baclofen, beclomethsone, benezepril, benzonatate, betamethasone, bicalutanide, boceprevir, budesonide, bupropion, busulphan, butenafine, calcifediol, calciprotiene, calcitriol, camptothecan, candesartan, capsaicin, carbamezepine, carotenes, celecoxib, cerivistatin, cetrizine, chlorpheniramine, cholecalciferol, cilostazol, cimetidine, cinnarizine, ciprofloxacin, cisapride, clarithromycin, clemastine, clomiphene, clomipramine, clopidrogel, codeine, coenzyme Q10, cyclobenzaprine, cyclosporine, danazol, dantrolene, dexchlorpheniramine, diclofenac, dicoumarol, digoxin, dihydroepiandrosterone, dihydroergotamine, dihydrotachysterol, dirithromycin, donepezil, efavirenz, eposartan, ergocalciferol, ergotamine, essential fatty acid sources, etodolac, etoposide, famotidine, fenofibrate, fentanyl, fexofenadine, finasteride, flucanazole, flurbiprofen, fluvastatin, fosphenytion, frovatriptan, furazolidone, gabapentin, gemfibrozil, glibenclamide, glipizide, glyburide, glymepride, griseofulvin, halofantrine, ibuprofen, irbesartan, irinotecan, isosorbide, isotreinoin, itraconazole, ivermectin, ketoconazole, ketorolac, lamotrigine, lanosprazole, leflunomide, lisinopril, loperamide, loratadine, lovastatin, L-thryroxine, lutein, lycopene, medroxyprogesterone, mefepristone, mefloquine, megesterol, metaxalone, methadone, methoxsalen, metronidazole, metronidazole, miconazole, midazolam, miglitol, minoxidil, mitoxantrone, montelukast, nabumetone, nalbuphine, naratiptan, nelfinavir, nifedipine, nilsolidipine, nilutanide, nitrofurantoin, nizatidine, omeprazole, oprevelkin, osteradiol, oxaprozin, paclitaxel, paricalcitol, paroxetine, pentazocine, pioglitazone, pizofetin, pravastatin, prednisolone, probucol, progesterone, pseudoephedrine, pyridostigmine, rabeprazole, raloxifene, refocoxib, repaglinide, rifabutine, rifapentine, rifaximine, rimexolone, ritanovir, rivaroxaban, rizatriptan, rosiglitazone, saquinavir, sertraline, sibutramine, sildenafil, simvastatin, sirolimus, spironolactone, sumatriptan, tacrine, tacrolimus, tamoxifen, tamsulosin, targretin, tazarotene, telaprevir, telmisartan, teniposide, terbinafine, terzosin, tetrahydrocannabinol, tiagabine, ticlidopine, tirofibran, tizanidine, topiramate, topotecan, toremifene, tramadol, tretinoin, troglitazone, trovafloxacin, ubidecarenone, valsartan, venlafaxine, vertoporfin, vigabatrin, vitamin A, vitamin D, vitamin E, vitamin K, zafirlukast, zileuton, ziprasidone, zolmitriptan, zolpidem, and zopiclone, or a pharmaceutically acceptable salt, ester, or solvate thereof.

In other embodiments, a surfactant is a docusate salt or sodium lauryl sulfate.

In still other embodiments a water-soluble polymer is a hydroxypropyl methylcellulose, hydroxyethyl cellulose, or hydroxypropyl cellulose.

In other embodiments a size reduction procedure comprises homogenization, ball milling, or fixed-geometry fluid processing.

In one embodiment of the invention the aqueous solvent is removed from the pharmaceutical composition to form a dry powder. In still another embodiment the formed dry powder is loaded into a capsule.

In some embodiments, the pharmacologically inert cores are microcrystalline cellulose or sugar spheres.

In other embodiments, the particle-coated cores further have a coating comprising a polymer.

Still other embodiments comprise particle-coated cores further have a seal-coating comprising a pH-independent polymer.

In further embodiments the coated particulates are blended with pharmaceutical excipients and loaded into a capsule or compressed into a tablet.

One embodiment for preparing a pharmaceutical composition comprises: 1) subjecting an aqueous medium containing suspended drug particles, a water-soluble surfactant, and a water-soluble polymer to a particle size reduction procedure; 2) adding a second ionic polymer to the suspension after particle size reduction; and 3) coating the final suspension from 2) onto solid pharmacologically inert cores.

In some embodiments, the drug exhibits supersaturation solubility.

In other embodiments, the drug exhibits supersaturation solubility in a pH environment corresponding to a gastrointestinal absorption site for the drug.

In still further embodiments, the bioavailability of the drug after oral administration of the formulation to a subject is higher than bioavailability after administration of the drug in its original form.

Another embodiment is a method of treating a patient comprising administering the nanosuspension. A further embodiment is a method of treating a patient comprising administering a pharmaceutical composition of an inert particulate solid support coated with the nanosuspension to form a coated particulate, the composition further comprising at least one additive, excipient, or carrier.

DETAILED DESCRIPTION

The present disclosure provides pharmaceutical dosage forms containing a particulate active ingredient. In embodiments, an active pharmaceutical ingredient that is present has limited or no appreciable solubility in USP defined media and at physiological pH values. Water solubility of the non-ionized form at room temperature for such active ingredients generally are less than about 10 mg/mL, and frequently less than about 1 mg/mL or less than about 0.1 mg/mL. Such active ingredients are sometimes referred to as "hydrophobic drugs."

In aspects, this disclosure includes: 1) processes of making nanoparticle suspensions; and 2) converting a nanoparticle suspension into a solid pharmaceutical dosage form comprising nanoparticles of hydrophobic drug embedded in a polymer. Embodiments of dosage forms exhibit the features of maintaining the primary drug particle sizes of the suspensions after downstream processing into solid dosage forms and also maintaining a supersaturation solubility profile.

Examples of suitable active ingredients include, but are not limited to, members of the therapeutic categories analgesics, anti-inflammatory agents, anthelmintics, anti-arrhythmic agents, anti-bacterial agents, anti-viral agents, anticoagulants, anti-depressants, anti-diabetic agents, anti-epileptic agents, anti-fungal agents, anti-gout agents, anti-hypertensive agents, anti-malarial agents, anti-migraine agents, anti-muscarinic agents, anti-neoplastic agents, erectile dysfunction improving agents, immunosuppressants, anti-protozoa agents, anti-thyroid agents, anti-anxiolytic agents, sedatives, hypnotics, neuroleptics, β-blockers, cardiac inotropic agents, corticosteroids, diuretics, anti-Parkinsonian agents, gastrointestinal agents, histamine receptor antagonists, keratolytics, lipid regulating agents, anti-angina agents, cox-2 inhibitors, leucotriene inhibitors, macrolides, muscle relaxants, nutritional agents, opioid analgesics, protease inhibitors, sex hormones, stimulants, anti-osteoporosis agents, anti-obesity agents, cognition enhancers, anti-urinary incontinence agents, nutritional oils, anti-benign prostate hypertrophy agents, essential fatty acids, non-essential fatty acids, and any combinations of two or more thereof.

Specific examples of suitable active ingredients include, but are not limited to: abiraterone, acutretin, albendazole, albuterol, aminogluthemide, amiodarone, amlodipine, amphetamine, amphotericin B, atorvastatin, atovaquone, azithromycin, baclofen, beclomethsone, benezepril, benzonatate, betamethasone, bicalutanide, boceprevir, budesonide, bupropion, busulphan, butenafine, calcifediol, calcirotiene, calcitriol, camptothecan, candesartan, capsaicin, carbamezepine, carotenes, carvedilol, celecoxib, cerivistatin, cetrizine, chlorpheniramine, cholecalciferol, cilostazol, cimetidine, cinnarizine, ciprofloxacin, cisapride, clarithromycin, clemastine, clomiphene, clomipramine, clopidrogel, codeine, coenzyme Q10, cyclobenzaprine, cyclosporine, danazol, dantrolene, dexchlopheniramine, diclofenac, dicoumarol, digoxin, dihydroepiandrosterone, dihydroergotamine, dihydrotachysterol, dirithromycin, donepezil, efavirenz, eposartan, ergocalciferol, ergotamine, essential fatty acid sources, etodolac, etoposide, famotidine, fenofibrate, fentanyl, fexofenadine, finasteride, flucanazole, flurbiprofen, fluvastatin, fosphenytion, frovatriptan, furazolidone, gabapentin, gemfibrozil, glibenclamide, glipizide, glyburide, glymepride, griseofulvin, halofantrine, ibuprofen, irbesartan, irinotecan, isosorbide, isotreinoin, itraconazole, ivermectin, ketoconazole, ketorolac, lamotrigine, lanosprazole, leflunomide, lisinopril, loperamide, loratadine, lovastatin, L-thryroxine, lutein, lycopene, medroxyprogesterone, mefepristone, mefloquine, megesterol, metaxalone, methadone, methoxsalen, metronidazole, metronidazole, miconazole, midazolam, miglitol, minoxidil, mitoxantrone, montelukast, nabumetone, nalbuphine, naratiptan, nelfinavir, nifedipine, nilsolidipine, nilutanide, nitrofurantoin, nizatidine, omeprazole, oprevelkin, osteradiol, oxaprozin, paclitaxel, paricalcitol, paroxetine, pentazocine, pioglitazone, pizofetin, pravastatin, prednisolone, probucol, progesterone, pseudoephedrine, pyridostigmine, rabeprazole, raloxifene, refocoxib, repaglinide, rifabutine, rifapentine, rifaximine, rimexolone, ritanovir, rivaroxaban, rizatriptan, rosiglitazone, saquinavir, sertraline, sibutramine, sildenafil, simvastatin, sirolimus, spironolactone, sumatriptan, tacrine, tacrolimus, tamoxifen, tamsulosin, targretin, tazarotene, telaprevir, telmisartan, teniposide, terbinafine, terzosin, tetrahydrocannabinol, tiagabine, ticlidopine, tirofibran, tizanidine, topiramate, topotecan, toremifene, tramadol, tretinoin, troglitazone, trovafloxacin, ubidecarenone, valsartan, venlafaxine, vertoporfin, vigabatrin, vitamin A, vitamin D, vitamin E, vitamin K, zafirlukast, zileuton, ziprasidone, zolmitriptan, zolpidem, and zopiclone. This listing is not exhaustive, as many other drug substances can be used. Also, any of the pharmaceutically acceptable salts, esters, solvates, and other derivatives of the active ingredients that can deliver the drugs also can be used, in any polymorphic forms, and combinations of any two or more active ingredients can be used. In particular, many of these drug substances are commonly used in a salt or ester form, but the list above recites only the base drug, for purposes of brevity.

One aspect of the application involves the preparation of pharmaceutically active ingredient particulates having mean sizes less than 1 μm. In another embodiment the pharmaceutically active ingredient particulates have mean sizes of less than about 800 nm. In a further embodiment the pharmaceutically active ingredient particulates have mean sizes of less than about 500 nm. Particles with sizes less than 1 μm in their largest dimension are "nanoparticles." In some embodiments, nanoparticles can be prepared by subjecting an aqueous medium containing suspended drug particles, a water-soluble surfactant, and a water-soluble polymer to a particle size reduction procedure.

Suitable water-soluble surfactants include, but are not limited to, members from the following types: ionic surfactants, such as the anionic materials sodium lauryl sulfate, sodium laureth sulfate, dioctyl sodium (or potassium) sulfosuccinate ("docusate" salts), and sodium stearate, and the cationic materials such as cetylpyridinium chloride and lecithin; and nonionic materials such as cetyl alcohol, stearyl alcohol, cetostearyl alcohol, glycerol alkyl esters such as glyceryl laurate, polyoxyethylene glycol sorbitan alkyl esters (polysorbates), sorbitan alkyl esters (e.g., SPAN® products), cocoamide MEA, cocoamide DEA, dodecyldimethylamine oxide, and block copolymers of polyethylene glycol and polypropylene glycol (poloxamers).

Suitable water-soluble polymers include both solution formers and polymeric substances that do not form true solutions, but swell upon contact with water to form colloidal dispersions having the appearance of solutions. Representative members include, but are not limited to: cellulose ethers, such as methylcelluloses having nominal viscosities in the range of about 3 to about 5000 mPa·s, hydroxyethyl celluloses having nominal viscosities in the range of about 3 to about 5000 mPa·s, hydroxyethylmethyl celluloses having nominal viscosities in the range of about 100 to 70000 mPa·s, hydroxypropyl celluloses ("HPC") having nominal viscosities in the range of about 10 to about 5000 mPa·s, and hydroxypropyl methylcelluloses (hypromelloses or "HPMC"), of various grades such as "E", "F", and "K," having nominal viscosities in the range of about 1 to about 20000 mPa·s; polyvinylpyrrolidones (povidones or "PVP") having nominal molecular weights in the range of about 4000 to about 1,300,000; copovidone; macrogols having molecular weights in the range of about 400 to about 8000; graft copolymers of polyvinyl alcohols and macrogols; polyvinyl caprolactam-polyvinyl acetate-polyethylene glycol graft copolymers; and polymethacrylates (i.e., copolymers of acrylic and methacrylic acid esters). The viscosities are usually measured using a 2% by weight aqueous solution, at 20° C.

Those skilled in the art will appreciate that commercially available products in these categories having chain lengths and substituents that provide the desired water solubility.

Suitable particle size reduction procedures can involve the use of equipment such as ball mills, rotor-stator colloid mills, homogenizers, jet mills, ultrasonic cavitation mills, and fixed-geometry fluid processors. An example of a fixed-geometry fluid processor is a MICROFLUIDIZER™, sold by Microfluidics Corporation of Newton, Mass. USA, that forces a fluid under very high pressure through microchannels into an interaction chamber, where two opposing streams of the fluid collide and then are conducted out of the chamber approximately perpendicular to the collision plane; the outlet fluid can be collected and recirculated through the interaction chamber, until desired particle sizes are obtained.

After the particle size reduction procedure, a suspension containing very small particles of the drug or drugs may be obtained.

The prepared suspensions can be further combined with a second polymeric substance (a de-agglomeration agent, defined herein), to further stabilize the very small particles. While the present disclosure should not be bound to any particular theoretical explanations, it is believed that the presence of an ionic polymer, a "de-agglomeration agent", inhibits drug particle agglomeration that would alter the particle size distributions over time when the suspensions are stored and/or further processed into pharmaceutical dosage forms.

Useful polymers include, but are not limited to, any one or more of materials described below as "ionic polymers" and any other polymers described herein. Various ionic polymers for use in the present application include, but are not limited to, EUDRAGIT™ L100 and E100 (polymers and copolymers of acrylic and methacrylic acids), cellulose acetate butyrates, cellulose acetate phthalates, hydroxypropyl methylcellulose phthalates and succinates, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), and any mixtures of two or more thereof.

Among the useful polymers are polymethacrylates, such as various products of Evonik Industries sold as EUDRAGIT™ copolymers, and hydrophobic cellulose ether derivatives, such as hypromellose acetate succinates.

EUDRAGIT L 100-55 is an anionic copolymer based on methacrylic acid and ethyl acrylate, described in the USP as "methacrylic acid copolymer, Type C" and having the following repeating unit.

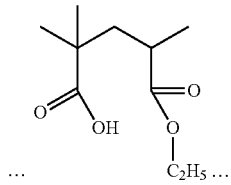

Polymethacrylate products are available in various physical forms, for example, EUDRAGIT L 30 D-55 being an aqueous dispersion form of EUDRAGIT L 100-55. Polymer products similar to the EUDRAGIT products are available from other sources.

Hypromellose acetate succinate is a pH-dependent polymer and is available from Shin-Etsu Chemical Co. as AQOA™ products. It is a mixture of acetic acid and monosuccinic acid esters of hydroxypropyl methylcellulose. The USP specification requires that it contain from 12.0 to 28.0 percent of methoxy groups, from 4.0 to 23.0 percent of hydroxypropyl groups, from 2.0 to 16.0 percent of acetyl groups, and from 4.0 to 28.0 percent of succinoyl groups, calculated on the dry basis. The commercially available AQOAT AS-LF product grade contains 8% acetyl groups and 15% succinoyl groups, AQOAT AS-MF contains 9% acetyl groups and 11% succinoyl groups, AQOAT AS-HF contains 12% acetyl groups and 6% succinoyl groups, and each of these products has a mean particle size of 5 µm.

It is believe that aggregation of nanoparticles may occur during down-stream processing or long-term storage. It is critical to ensure that the nanoparticles are maintained in a pharmaceutical formulation for improved dissolution. The selection of a suitable stabilizer and its optimal concentration are very important for stabilizing the smaller size particles and to maintain the shelf life stability of the final product. The stabilization of smaller particles is more critical than creating them. Interactions between the newly formed particles and the surface stabilizer molecules play a crucial role in the stabilization process. If the interparticular affinity is greater than the affinity of a particle and a surface stabilizer, aggregation is favored; otherwise aggregation is lowered or can be completely inhibited. The particle aggregation affects the long-term stability of the drug nanocrystal formulations; particle aggregation mostly depends on the stabilizer, its type and concentration used.

Ionic polymers have been used for enteric or delayed release coating application, amorphous solid dispersion stabilization. It has now been unexpectedly discovered that these ionic polymers can be used as de-agglomeration agents for nanoparticle stabilization when added into a nano-suspension to prevent aggregates of nanoparticles during down-stream processing (i.e., nano-suspension layered onto non-pareil seeds, top-spraying granulation, spray drying) into pharmaceutical dosage forms. These ionic polymers stabilize the nano-formulation and permit the formulation to be maintained at a supersaturated level in the gastrointestinal tract. The ratio of the pharmaceutically active ingredient to the de-agglomeration agent is in the range of 20:1 to 1:20. In another embodiment, ratio of the pharmaceutically active ingredient to the de-agglomeration agent is in the range of 5:1 to 1:5. In another embodiment, ratio of the pharmaceutically active ingredient to the de-agglomeration agent is in the range of 3:1 to 1:3.

The concept of supersaturation has been described in the literature, such as by J. Brouwers et al, "Supersaturating Drug Delivery Systems: The Answer to Solubility-Limited Oral Bioavailability?" *Journal of Pharmaceutical Sciences*, Vol. 98(8), pages 2549-2572, 2009. Supersaturation is an enhanced solubility of a metastable higher-energy form of a drug, as compared to the saturation solubility of the lowest energy state of the drug. Maintenance of the supersaturation condition in areas of the gastrointestinal tract where drug absorption occurs can provide increased bioavailability, for an improved therapeutic effect.

The stabilized nano-formulation is capable to provide and maintain a pharmaceutically active agent in a supersaturated state. In some embodiments the supersaturation of the pharmaceutically active agent is maintained at 101% to 1000%. In another embodiment the supersaturation of the pharmaceutically active agent is maintained at 101% to 500%. In another embodiment the supersaturation of the pharmaceutically active agent is maintained at 101 to 200%.

The suspensions can be packaged directly for use as fluid products, with the optional addition of any number of suitable excipients such as a viscosity modifier, preservative, and/or flavoring and coloring agent, can be further processed to prepare solid dosage forms, or the particulate content can be separated (e.g., by evaporating the liquid component) and used to prepare solid dosage forms. Suitable solid unit doses include various capsule and tablet dosage forms.

To inhibit microbial growth during processing, one or more preservatives can be included. For example, a preservative can be added during or after particle size reduction, in order to inhibit microbial growth during processing and storage of drug-containing suspensions, and prior to converting into solid dosage forms. In embodiments, useful amounts range from about 0.001 to about 10 weight percent of the active agent content. Examples of such preservatives include, but are not limited to, benzoic acid and its salts such as sodium benzoate, methylparaben, propylparaben, and sorbic acid and its salts.

In embodiments of solid dosage form preparation, a drug-containing fluid is coated onto solid pharmacologically inert particulate supports. Useful particulate supports include, without limitation, those made from sucrose, lactose, mannitol, starches, calcium phosphate, cellulose, etc. Frequently, a particulate support will be generally spherical in shape, although this is not essential. Among the useful substances are microcrystalline cellulose spheres that are available in various particle size ranges as CELLETS™ (from Pharmatrans Sanaq AG, Switzerland) and CELPHERE™ (Asahi Kasei Group, Japan) products. Tartaric acid pellets can be used as a substrate, such as to promote solubility of basic drugs by creating an acidic pH environment in the presence of gastrointestinal tract fluids.

A suspension can be coated onto particulate supports by any means known in the art, including spraying or such as using a fluidized bed granulator. After removal of the suspension vehicle, the particulates can optionally be coated, such as with a protective polymer seal-coating or a drug-release modifying polymer, and then filled into capsules or formulated into tablets. Depending on the polymer that is used for seal-coating, it can be applied as a dispersion or solution in an aqueous fluid, a hydro-alcoholic fluid, or an organic liquid, optionally further containing at least one coating excipient such as a plasticizer, buffer, etc.

To prepare tablets, additional excipients (such as any of those described further below), for example, microcrystalline cellulose, dibasic calcium phosphate, and/or lactose monohydrate, can be added to provide mechanical strength to compressed tablets. The drug-containing particulates can be combined with any number of desired excipients, with or without a granulation step, and the mixture can be compressed into tablets.

Alternatively, the solvent can be removed from a suspension, and the resulting powder can be processed into any desired solid dosage form. Such processing can include wet or dry granulation and compressing into tablets or filling into capsules.

Solid dosage units contain one or more drug substances, together with any desired number of excipients, such as, but not limited to, one or more of diluents, binders, drug stabilizers, disintegrants, glidants, lubricants, release rate modifiers, preservatives, antioxidants, coatings, colorants, flavoring agents, etc.

Various useful fillers or diluents according to the present application include, but are not limited to, starches, lactose, cellulose derivatives, confectioner's sugar and the like. Various grades of lactose include, but are not limited to, lactose monohydrate, lactose DT, lactose anhydrous, and others. Different starches include, but are not limited to, maize starch, potato starch, rice starch, wheat starch, pregelatinized starch, and others. Different cellulose compounds that can be used include crystalline cellulose and powdered cellulose. Other useful diluents include, but are not limited to, carmellose, sugar alcohols such as mannitol, sorbitol, and xylitol, calcium carbonate, magnesium carbonate, dibasic calcium phosphate, and tribasic calcium phosphate.

Various useful binders according to the present application include, but are not limited to, hydroxypropylcelluloses in various grades, hydroxypropyl methylcelluloses (e.g., METHOCEL™ products) and useful in various grades, polyvinylpyrrolidones (such as grades K25, K29, K30, and K90), copovidones (e.g., PLASDONE™ S 630), powdered *acacia*, gelatin, guar gum, carbomers (e.g., CARBOPOL™ products), methylcelluloses, polymethacrylates, and starches.

Various useful disintegrants include, but are not limited to, carmellose calcium, carboxymethylstarch sodium, croscarmellose sodium, crospovidones, examples of commercially available crospovidone products including but not limited to crosslinked povidones, KOLLIDON™ CL from BASF (Germany), POLYPLASDONE™ XL, XI-10, and INF-10 from ISP Inc. (USA), and low-substituted hydroxypropylcelluloses. Examples of low-substituted hydroxypropylcelluloses include, but are not limited to, low-substituted hydroxypropylcellulose LH11, LH21, LH31, LH22, LH32, LH2O, LH30, LH32 and LH33 (all supplied by Shin-Etsu Chemical Co., Ltd.). Some other useful disintegrants include sodium starch glycolate, colloidal silicon dioxide, and various starches.

In embodiments, formulations of the present application contain at least one antioxidant, for enhancing the stability of a drug. The antioxidant may be present either as a part of the composition or a packaging component. Thus, in a particular embodiment, antioxidants are introduced into the formulation during a drug loading stage over inert cores. The antioxidants are present in amounts effective to retard decomposition of the drug that is susceptible to oxidation. In embodiments, the content of an antioxidant in the formulations ranges from about 0.001 to 10 weight percent, with respect to the active agent content. Non-limiting examples of antioxidants include one or more of ascorbic acid and its salts, tocopherols, sulfite salts such as sodium metabisulfite or sodium sulfite, sodium sulfide, butylated hydroxyanisole, butylated hydroxytoluene, ascorbyl palmitate, and propyl gallate. Other suitable antioxidants will be readily recognized by those skilled in the art.

Useful lubricants include magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, and any combinations thereof.

One or more glidant materials, which improve the flow of powder blends, pellets, etc. and minimize dosage form weight variations, can be used. Useful glidants include, but are not limited to, silicon dioxide, talc, kaolin, and combinations thereof.

Coloring agents can be used to color code compositions, for example, to indicate the type and dosage of the therapeutic agent therein. Coloring agents can also be used to differentiate the varied fractions of multi-particulates comprised in a unit dosage form such as a capsule. Suitable coloring agents include, without limitation, natural and/or artificial compounds such as FD&C coloring agents, natural juice concentrates, pigments such as titanium oxide, silicon dioxide, iron oxides, zinc oxide, any combinations thereof, and the like.

Solid pharmaceutical dosage forms may be provided with outer coatings that modify the release characteristics of the contained drug or drugs, after administration. Other types of coatings are merely cosmetic, or serve to protect the dosage forms during packaging, shipping, and use. The coatings typically comprise at least one pH-independent or pH-dependent soluble polymer as the major ingredient, frequently also including any one or more of various additives.

Useful additives for coatings include, but are not limited to, plasticizers, antiadherents, opacifiers, solvents, and optionally colorants, lubricants, pigments, antifoam agents, and polishing agents.

Various useful plasticizers include, but are not limited to, substances such as castor oil, diacetylated monoglycerides, dibutyl sebacate, diethyl phthalate, glycerin, polyethylene glycol, propylene glycol, triacetin, and triethyl citrate, and mixtures thereof. The type of plasticizer depends upon the type of coating agent. An opacifier such as titanium dioxide may also be present in amounts ranging from about 0.5-20%, based on the total weight of the coating.

Anti-adhesives are frequently used in film coating processes to avoid sticking effects during film formation and drying. An example of a useful anti-adhesive for this purpose is talc. An anti-adhesive is frequently present in the film coating in amounts about 0.5-15%, based upon the total weight of the coating.

Various solvents that can be used in processes of preparing pharmaceutical formulations of the present application include, but are not limited to, water, methanol, ethanol, acetone, diacetone, polyols, polyethers, oils, esters, alkyl ketones, methylene chloride, isopropyl alcohol, butyl alcohol, methyl acetate, ethyl acetate, isopropyl acetate, castor oil, ethylene glycol monoethyl ether, diethylene glycol monobutyl ether, diethylene glycol monoethyl ether, dimethylsulfoxide, N,N-dimethylformamide, tetrahydrofuran, and any mixtures thereof.

The foregoing lists of excipient substances are not exhaustive, but are representative of members of the various categories. Those skilled in the art will be aware of many other useful substances, and their use is specifically contemplated herein. Also, it is well-known that many excipients can serve more than one purpose in pharmaceutical formulations.

Particle sizes of powders and suspended powders may be determined using any of conventional technologies, including optical microscopy, Coulter Counter™ electrical zone sensing methods, laser light diffraction (such as with equipment sold by Malvern Instruments Ltd. and Horiba Instruments, Inc.), etc. Particle size distributions frequently are represented by terms such as $D_{10}$, $D_{50}$, $D_{90}$, and the like, where the numerical portion is the volume percentage of measured particles having a dimension that does not exceed the given size. For example, $D_{50}$=400 nm means that 50 percent of the particles have sizes that do not exceed 400 nm in any dimension. Suspended particle sizes optionally can be measured using various physiological media to form the suspensions, e.g., simulated gastric fluid (pH 1.2), acetate buffer (pH 4.5) and simulated intestinal fluid (pH 5.5-7.5), or using water or a buffered or unbuffered aqueous medium.

Pharmaceutical products can be tested for their drug dissolution characteristics, such as using test 711 "Dissolution" in United States Pharmacopeia 24, United States Pharmacopeial Convention, Inc., Rockville, Md., 1999 ("USP"). Various fluids can be used as the dissolution media, including acids, buffers, simulated digestive tract fluids, etc., and many of these are defined in various monographs of the USP. An example of a procedure uses "Apparatus 2," which has a vessel containing a medium that is stirred with a rotating paddle. Typically, a dosage unit is immersed into the medium and samples of the medium are withdrawn at intervals for drug content analysis, frequently using high performance liquid chromatography ("HPLC") techniques.

The following examples further describe certain specific aspects and embodiments of the disclosure, are provided only for purposes of illustration, and should not be construed as limiting the scope of the disclosure in any manner.

EXAMPLES 1-4

Dispersions were prepared using the listed ingredients, where the percentages are by weight.

TABLE 1

| Example 1 | Example 2 | Example 3 | Example 4 |
|---|---|---|---|
| Progesterone (10%) | Progesterone (10%) | Metaxalone (10%) | Metaxalone (10%) |
| HPMC* (2%) | HPC** (2%) | HPMC* (2%) | HPC** (2%) |
| Docusate sodium (0.1%) | Sodium lauryl sulfate (0.1%) | Docusate sodium (0.1%) | Sodium lauryl sulfate (0.1%) |
| Water (q.s. to 100%) | Water (q.s. to 100%) | Water (q.s. to 100%) | Water (q.s. to 100%) |

*e.g., METHOCEL ® E5 LV, a product of Dow Chemical Co.
**e.g., KLUCEL ® LF, a product of Aqualon Div., Hercules Incorporated.

Procedure:

1. HPMC or HPC was mixed with water until dissolved, then docusate sodium or sodium lauryl sulfate was added and the solution was mixed for another 60 minutes.

2. Progesterone or metaxalone was added to the polymer solution and mixed, followed by homogenization for 30-60 minutes. The dispersion was mixed for an additional 60 minutes to obtain a uniform dispersion. Approximately 1 L quantities of dispersions prepared according to Examples 1-4 were processed in a laboratory-scale Model 120B MICROFLUIDIZER® (from Microfluidics, a division of IDEX Corporation). The device, connected to a 345-690 kPa (50-100 psi) air supply, is adjusted to produce a fluid pressure of 69,000-175,000 kPa (10,000-25,000 psi). The machine base, interaction chamber and piping of the Micofluidizer device are maintained below 30° C. by circulating chilled water. The dispersions were passed through the MICROFLUIDIZER interaction chamber and the produced suspensions were returned to the top, and side, of the bulk chamber. The suspensions were recirculated continuously through the interaction chamber, and samples were taken at time intervals for analysis of particle sizes.

Prepared suspensions (10 µL) were diluted to 1 mL with a pH 6.8 phosphate buffer, 50 mM. The diluted suspensions were maintained under constant stirring and particle sizes were measured at time intervals using a Malvern ZETA-SIZER™ dynamic light scattering analyzer. Results are shown in Table 2.

TABLE 2

| Suspension | Mean Primary Particle Size (nm) | | | | |
|---|---|---|---|---|---|
| | 0 minutes | 10 minutes | 30 minutes | 60 minutes | 90 minutes |
| Example 1 | 540 | 500 | 510 | 520 | 535 |
| Example 2 | 365 | 344 | 360 | 250 | 355 |
| Example 3 | 282 | 288 | 280 | 284 | 286 |
| Example 4 | 334 | 330 | 335 | 318 | 315 |

The prepared suspensions have stable particle sizes after dilution.

EXAMPLE 5

A progesterone suspension, prepared according to the general procedure of Example 1 with HMPC and docusate sodium, was combined with various secondary ionic polymers, in a weight ratio of 60 parts suspension to 40 parts secondary ionic polymer, and stirred for 30 minutes. The mixtures were poured into aluminum foil trays and were dried at 38° C. for 1-2 days to create films. For each composition, some of the foil trays were further "aged" by storing open to the atmosphere for two weeks at 40° C. and 75% relative humidity. Films were separated from the trays, crushed into powders using a mortar and pestle or any type of milling mechanism, and passed through a 60 mesh sieve. Approximately 50 mg of the powder was added to 35 mL of phosphate buffer solution (pH 6.8; 50 mM) and mixed for 6 minutes to dissolve the polymer, then particle sizes were measured at time intervals (0, 10, 30, 60 and 90 minutes) using 1 mL samples.

The following table shows the results of particle size analyses for the progesterone suspensions, stabilized by combining the nanosuspension with various secondary ionic polymers. Surprisingly, the nanosuspensions containing a secondary ionic polymer (5B, 5E, and 5F) have much lower mean primary particle sizes. This illustrates that the addition of an ionic polymer after particle size reduction, provides further de-agglomeration of primary particles in the buffer and stabilizes them in the solid state. Even after storing samples at the accelerated stability testing conditions, the sizes of particles are maintained and no evidence of particle agglomeration is observed. Results are shown in Table 3.

TABLE 3

| Suspension | Polymer | Time (min.) | Mean Primary Particle Size (nm) | |
|---|---|---|---|---|
| | | | Initial Sample | Aged Sample |
| 5A (Comparative Example) | None | 10 | 910 | — |
| | | 30 | 900 | — |
| | | 60 | 930 | — |
| | | 90 | 940 | — |
| 5B (Ionic Polymer) | Methacrylic acid copolymer Type C (as the dispersion EUDRAGIT L 30 D-55) | 10 | 700 | 875 |
| | | 30 | 710 | 1000 |
| | | 60 | 707 | 975 |
| | | 90 | 730 | 930 |
| 5C (Comparative Example: Non-ionic polymer) | Graft copolymer of polyethylene glycol, polyvinylcaprolactam, and polyvinylacetate (SOLUPLUS ®) | 10 | 2000 | 2300 |
| | | 30 | 2100 | 860 |
| | | 60 | 2200 | 720 |
| | | 90 | 2100 | 1450 |
| 5D (Comparative Example: Non-ionic polymer) | Hypromellose (METHOCEL E5) | 10 | 960 | 745 |
| | | 30 | 1020 | 990 |
| | | 60 | 1040 | 790 |
| | | 90 | 1020 | 784 |
| 5E (Ionic polymer) | Methacrylic acid copolymer Type C (EUDRAGIT L 100-55) | 10 | 669 | 765 |
| | | 30 | 640 | 950 |
| | | 60 | 680 | 745 |
| | | 90 | 650 | 740 |
| 5F (Ionic Polymer) | Hypromellose acetate succinate LF (AQUOT LF) | 10 | 507 | 506 |
| | | 30 | 505 | 510 |
| | | 60 | 450 | 505 |
| | | 90 | 465 | 530 |

EXAMPLE 6

A metaxalone suspension, prepared according to the general procedure of Example 3 with HPMC and docusate sodium, was combined with various secondary ionic polymers, in a weight ratio of 70 parts suspension to 30 parts of the secondary ionic polymer, and stirred for 30 minutes. The mixtures were poured into aluminum foil trays and were dried at 38° C. for 1-2 days. For each composition, some of the foil trays were further aged by storing open to the atmosphere for two weeks at 40° C. and 75% relative humidity. The solids were separated from the foil, crushed into powders, and passed through a 60 mesh sieve. Approximately 50 mg of the powder was added to 35 mL of phosphate buffer solution (pH 6.8; 50 mM) and mixed for 6 minutes to dissolve the polymer, then mean primary particle sizes were measured at time intervals (0, 10, 30, 60, and 90 minutes) by withdrawing 1 mL samples.

The following table shows the results of particle size analyses for the metaxalone suspensions, stabilized by combining with the various ionic and nonionic polymers. Surprisingly, the nanosuspensions containing ionic polymers (6c-6F) have lower mean primary particle sizes. This illustrates that the addition of an ionic polymer after particle size reduction provides further de-agglomeration of the primary particles in the buffer and stabilizes them in the solid state. Even after storing samples under the accelerated stability testing conditions, the sizes of particles are stable and no evidence of particle agglomeration is observed. Results are shown in Table 4.

TABLE 4

| Suspension | Polymer | Time (min.) | Mean Primary Particle Size (nm) Initial Sample | Mean Primary Particle Size (nm) Aged Sample |
|---|---|---|---|---|
| 6A (Comparative Example) | None | 10 | 1698 | — |
|  |  | 30 | 1828 | — |
|  |  | 60 | 1634 | — |
|  |  | 90 | 1645 | — |
| 6B (Comparative Example: Non-ionic Polymer) | Hypromellose (METHOCEL E5) | 10 | 511 | 584 |
|  |  | 30 | 517 | 549 |
|  |  | 60 | 504 | 493 |
|  |  | 90 | 516 | 477 |
| 6C (Ionic Polymer) | Hypromellose acetate succinate LF (AQUOT LF) | 10 | 409 | 423 |
|  |  | 30 | 404 | 409 |
|  |  | 60 | 412 | 400 |
|  |  | 90 | 400 | 389 |
| 6D (Ionic Polymer) | Hypromellose acetate succinate MF (AQUOT MF) | 10 | 497 | 483 |
|  |  | 30 | 485 | 462 |
|  |  | 60 | 477 | 473 |
|  |  | 90 | 467 | 455 |
| 6E (Ionic polymer) | Hypromellose acetate succinate HF (AQUOT HF) | 10 | 609 | 636 |
|  |  | 30 | 590 | 617 |
|  |  | 60 | 587 | 623 |
|  |  | 90 | 587 | 612 |
| 6F (Ionic polymer) | Methacrylic acid copolymer Type C (EUDRAGIT L 100-55) | 10 | 402 | 413 |
|  |  | 30 | 396 | 415 |
|  |  | 60 | 411 | 404 |
|  |  | 90 | 416 | 410 |

EXAMPLE 7

Metaxalone suspensions prepared in Example 6 were tested for their drug dissolution characteristics. Approximately 1 g of a suspension was placed in a 50 mL conical flask, 50 mL of 50 mM phosphate buffer (pH 6.8) was added, then the mixture was vortexed and incubated at 37° C. with continuous shaking. Samples 5 mL) were withdrawn at intervals, filtered through a Whatman syringe filter (PVDF, 0.45 μm), diluted 1:1 by volume with phosphate buffer, mixed well and vortexed. When the solution was not clear, it was filtered through a 0.22 μm filter. The filtrate was diluted with an equal volume of acetonitrile prior to HPLC analysis for its metaxalone content, giving the results in the table below.

HPLC Conditions for Metaxalone Analysis:
Column: BDS Hypersil C18, 250×4.6 mm, 5 μm;
Detector wavelength: 230 nm;
Mobile Phase: a mixture of acetonitrile, methanol, and water (26:31:43 parts by volume, respectively);
Flow rate: 1.0 mL/minute;
Injection volume: 20 μL;
Column temperature: 40° C.;
Sample temperature: 25° C.;
Run time: 10 minutes.

TABLE 5

| | Metaxalone Concentration, mg/mL | | | | | |
|---|---|---|---|---|---|---|
| Minutes | 6A | 6B | 6C | 6D | 6E | 6F |
| 0 | 0 | 0 | 0 | 0 | 0 | 0 |
| 30 | 0.2997 | 0.3867 | 0.5602 | 0.8814 | 0.6571 | 0.6474 |
| 60 | 0.3022 | 0.4077 | 0.7058 | 0.9408 | 0.7380 | 0.9170 |
| 120 | 0.3073 | 0.3799 | 0.8259 | 1.0578 | 0.7393 | 1.1312 |

As seen in Table 5, the formulations containing an ionic polymer (6C-6F) in the nanosuspension had a much higher dissolution then the comparative examples (6A and 6B).

EXAMPLE 8

Progesterone suspensions prepared in Example 5 are tested for their drug dissolution characteristics. Sample containing approximately 60 mg of progesterone are placed into a 125 mL Erlenmeyer flask containing 50 mL of 50 mM phosphate buffer, (pH 6.8) previously equilibrated at 37° C. After swirling, the sample is incubated at 37° C. with continuous shaking. At intervals, 7 mL aliquots are withdrawn and filtered through a 0.45 mm PVDF filter, returning the first 5 mL of filtrate back to the flask and collecting the next 2 mL of filtrate for analysis. The filtrate sample is diluted with twice its volume of acetonitrile. However, if the filtrate is cloudy, the sample is centrifuged at 15,000 rpm for 10 minutes and the supernate is diluted. The diluted sample is used for HPLC analysis, giving the results in the table below.

HPLC Conditions:
Column type: Agilent Poroshell EC-120 C18, 4.6×100 mm, 2.7 μm;
Detector wavelength: 243 nm;
Flow rate: 1.0 mL/minute;
Injection volume: 50 μL;
Column temperature: 40° C.;
Sample temperature: ambient;
Run time: 18 minutes.

TABLE 6

| | Progesterone Concentration (mg/mL) | | | |
|---|---|---|---|---|
| Minutes | 5A | 5B | 5F | 5E |
| 0 | 0 | 0 | 0 | 0 |
| 30 | 0.0118 | 0.2505 | 0.2573 | 0.0427 |
| 60 | 0.0115 | 0.0192 | 0.2292 | 0.0314 |
| 120 | 0.0116 | 0.0167 | 0.4066 | 0.0500 |

For both metaxalone and progesterone, stabilized formulations maintain superior solubility over time, compared to the starting drug substances alone or their nanoparticle drug suspensions prepared in Example 1.

Pharmaceutical formulations were prepared, using the ingredients listed in the tables of Examples 9 and 10.

EXAMPLE 9

TABLE 7

| | mg/Capsule | | | | |
|---|---|---|---|---|---|
| Ingredient | 9A | 9B | 9C | 9D | 9E |
| Microcrystalline cellulose or sugar spheres | 150 | 150 | 150 | 150 | 150 |
| Drug Layering | | | | | |
| Progesterone | 100 | 100 | 100 | 100 | 100 |
| Hypromellose E5 | 19 | 19 | 19 | 19 | 19 |
| Docusate sodium | — | 1 | 1 | 1 | 1 |
| Hypromellose acetate succinate | 66.67 | 66.67 | — | 71.94 | 5.27 |
| Methacrylic acid copolymer type C | — | — | 66.67 | 15.81 | 82.48 |

TABLE 7-continued

| | mg/Capsule | | | | |
|---|---|---|---|---|---|
| Ingredient | 9A | 9B | 9C | 9D | 9E |
| Potassium phosphate (monobasic) | — | 17 | 17 | 17 | 17 |
| Final Blending | | | | | |
| Talc | 1.66 | 1.66 | 1.66 | 1.66 | 1.66 |
| Colloidal silicon dioxide | 1.67 | 1.67 | 1.67 | 1.67 | 1.67 |

EXAMPLE 10

TABLE 8

| | mg/Capsule | | | | |
|---|---|---|---|---|---|
| Ingredient | 10A | 10B | 10C | 10D | 10E |
| Microcrystalline cellulose or sugar spheres | 150 | 150 | 150 | 150 | 150 |
| Drug Layering | | | | | |
| Metaxalone | 200 | 200 | 200 | 200 | 200 |
| Hypromellose E5 | 38 | 38 | 38 | 38 | 38 |
| Docusate sodium | 2 | 2 | 2 | 2 | 2 |
| Hypromellose acetate succinate | 85.75 | — | 93.57 | 7.82 | 85.75 |
| Methacrylic acid copolymer type C | — | 85.75 | 23.45 | 109.2 | — |
| Triethyl citrate | — | — | 13.35 | 4.67 | — |
| Talc | — | — | 13.73 | 13.73 | — |
| Potassium phosphate (monobasic) | 21 | 21 | 21 | 21 | — |
| Final Blending | | | | | |
| Talc | 1.66 | 1.66 | 1.66 | 1.66 | 1.66 |
| Colloidal silicon dioxide | 1.67 | 1.67 | 1.67 | 1.67 | 1.67 |

Procedure for Examples 9 and 10:

A fluidized-bed granulator (Glatt GPCG-3) equipped with a 6-inch Wurster (bottom spray) insert was loaded with 0.75-1 kg of microcrystalline cellulose spheres (e.g., CEL-LETS® 500 from Pharmatrans Sanaq AG, having mean particle sizes of 500-710 µm), sugar spheres (or SUG-LETS® pellets made from sucrose and starch, from Color-con), or tartaric acid seeds (e.g., TAP 200 or 400 from Pharmatrans Sanaq AG). The particles were warmed with 35-45° C. dry inlet air. The fluidizing air volume was controlled by opening the exhaust air valve to approximately 50% of its maximum in the beginning, increasing to about 60% at the end of the spraying process. A previously prepared drug layering suspension (processed in a MICRO-FLUIDIZER apparatus using a suitable quantity of water, according to the procedure of a previous example), in a quantity containing the indicated amounts of drug, was sprayed onto fluidized spheres in the granulator. The dispersion was sprayed at an initial delivery rate of approximately 4-5 g/minute at an atomizing air pressure of about 200 kPa (2 bar). After delivery of about 30% of the spraying dispersion, the delivery rate was increased to 9-11 g/minute.

When the spraying process was completed, the coated spheres were dried with 40-60° C. dry inlet air for about 10 minutes. The coated spheres were then allowed to cool in the fluid bed with inlet air temperature of 20-25° C. for about 5-10 minutes. The dried drug coated spheres were sized using a 35 mesh sieve, and spheres passing through the sieve were discarded.

The spheres retained on the sieve were introduced into the fluidized-bed granulator equipped with the Wurster insert and warmed with 50-60° C. dry inlet air. A previously prepared functional coating dispersion (in a suitable quantity of water) was sprayed onto the fluidized spheres at a delivery rate of about 400 to 500 g/minute with atomizing air pressure of about 250 kPa (2.5 bar). When the spraying process was completed, the spheres were dried using 50-55° C. dry inlet air for about 10 minutes. The coated spheres were allowed to cool in the fluid bed using 20-25° C. dry inlet air, for about 5-10 minutes.

The seal-coated particles were blended with the "Final Blending" ingredients and were filled into hard gelatin capsules.

Pharmaceutical formulations may be prepared, using the ingredients in Examples 11-15.

EXAMPLE 11

TABLE 9

| | mg/Capsule | | | |
|---|---|---|---|---|
| Ingredient | 11A | 11B | 11C | 11D |
| Microcrystalline cellulose or sugar spheres | 150 | 150 | 150 | 150 |
| Drug Layering | | | | |
| Abiraterone acetate | 100 | 100 | 100 | 100 |
| Hypromellose E5 | 19 | 19 | 19 | 19 |
| Docusate sodium | 1 | 1 | 1 | 1 |
| Hypromellose acetate succinate | 66.67 | — | 71.94 | 5.27 |
| Methacrylic acid copolymer type C | — | 66.67 | 15.81 | 82.48 |
| Potassium phosphate (monobasic) | 17 | 17 | 17 | 17 |
| Final Blending | | | | |
| Talc | 1.66 | 1.66 | 1.66 | 1.66 |
| Colloidal silicon dioxide | 1.67 | 1.67 | 1.67 | 1.67 |

EXAMPLE 12

TABLE 10

| | mg/Capsule | | | |
|---|---|---|---|---|
| Ingredient | 12A | 12B | 12C | 12D |
| Microcrystalline cellulose or sugar spheres | 150 | 150 | 150 | 150 |
| Drug Layering | | | | |
| Telaprevir | 200 | 200 | 200 | 200 |
| Hypromellose E5 | 40 | 40 | 40 | 40 |
| Docusate sodium | 2 | 2 | 2 | 2 |
| Hypromellose acetate succinate | 85.75 | — | 93.57 | 7.82 |
| Methacrylic acid copolymer type C | — | 85.75 | 23.45 | 109.2 |
| Triethyl citrate | — | — | 13.35 | 4.67 |
| Talc | — | — | 13.73 | 13.73 |
| Potassium phosphate (monobasic) | 21 | 21 | 21 | 21 |

TABLE 10-continued

|  | mg/Capsule | | | |
| --- | --- | --- | --- | --- |
| Ingredient | 12A | 12B | 12C | 12D |
| Final Blending | | | | |
| Talc | 1.66 | 1.66 | 1.66 | 1.66 |
| Colloidal silicon dioxide | 1.67 | 1.67 | 1.67 | 1.67 |

EXAMPLE 13

TABLE 11

|  | mg/Capsule | | | |
| --- | --- | --- | --- | --- |
| Ingredient | 13A | 132B | 13C | 13D |
| Tartaric acid seeds | 75 | 75 | 75 | 75 |
| Drug Layering | | | | |
| Ziprasidone hydrochloride | 50 | 50 | 50 | 50 |
| Hypromellose E5 | 9.5 | 9.5 | 9.5 | 9.5 |
| Docusate sodium | 0.5 | 0.5 | 0.5 | 0.5 |
| Hypromellose acetate succinate | 33.33 | — | 36.00 | 2.6 |
| Methacrylic acid copolymer type C | — | 33.33 | 7.9 | 41.2 |
| Potassium phosphate (monobasic) | 8.5 | 8.5 | 8.5 | 8.5 |
| Final Blending | | | | |
| Talc | 0.8 | 0.8 | 0.8 | 0.8 |
| Colloidal silicon dioxide | 0.8 | 0.8 | 0.8 | 0.8 |

EXAMPLE 14

TABLE 12

|  | mg/Capsule | | | |
| --- | --- | --- | --- | --- |
| Ingredient | 14A | 14B | 14C | 14D |
| Microcrystalline cellulose or sugar spheres | 150 | 150 | 150 | 150 |
| Drug Layering | | | | |
| Boceprevir | 200 | 200 | 200 | 200 |
| Hypromellose E5 | 40 | 40 | 40 | 40 |
| Docusate sodium | 2 | 2 | 2 | 2 |
| Hypromellose acetate succinate | 85.75 | — | 93.57 | 7.82 |
| Methacrylic acid copolymer type C | — | 85.75 | 23.45 | 109.2 |
| Triethyl citrate | — | — | 13.35 | 4.67 |
| Talc | — | — | 13.73 | 13.73 |
| Potassium phosphate (monobasic) | 21 | 21 | 21 | 21 |
| Final Blending | | | | |
| Talc | 1.66 | 1.66 | 1.66 | 1.66 |
| Colloidal silicon dioxide | 1.67 | 1.67 | 1.67 | 1.67 |

EXAMPLE 15

TABLE 13

|  | mg/Capsule | | | |
| --- | --- | --- | --- | --- |
| Ingredient | 15A | 15B | 156C | 15D |
| Microcrystalline cellulose or sugar spheres | 15 | 15 | 15 | 15 |
| Drug Layering | | | | |
| Rivaroxaban | 20 | 20 | 20 | 20 |
| Hypromellose E5 | 4 | 4 | 4 | 4 |
| Docusate sodium | 0.2 | 0.2 | 0.2 | 0.2 |
| Hypromellose acetate succinate | 8.6 | — | 9.4 | 0.8 |
| Methacrylic acid copolymer type C | — | 8.6 | 2.3 | 10.9 |
| Triethyl citrate | — | — | 1.3 | 0.5 |
| Talc | — | — | 1.4 | 1.4 |
| Potassium phosphate (monobasic) | 2.1 | 2.1 | 2.1 | 2.1 |
| Final Blending | | | | |
| Talc | 0.17 | 0.17 | 0.17 | 0.17 |
| Colloidal silicon dioxide | 0.17 | 0.17 | 0.17 | 0.17 |

Procedure for Examples 11-15:

A fluidized-bed granulator (Glatt GPCG-3) equipped with a 6-inch Wurster (bottom spray) insert is loaded with 0.75-1 kg of microcrystalline cellulose spheres (e.g., CELLETS® 500 from Pharmatrans Sanaq AG, having mean particle sizes of 500-710 μm), sugar spheres (or SUGLETS® pellets made from sucrose and starch, from Colorcon), or tartaric acid seeds (e.g., TAP 200 or 400 from Pharmatrans Sanaq AG). The particles are warmed with 35-45° C. dry inlet air. The fluidizing air volume is controlled by opening the exhaust air valve to approximately 50% of its maximum in the beginning, increasing to about 60% at the end of the spraying process. A previously prepared drug layering suspension (processed in a MICROFLUIDIZER apparatus using a suitable quantity of water, according to the procedure of a previous example), in a quantity containing the indicated amounts of drug, is sprayed onto fluidized spheres in the granulator. The dispersion is sprayed at an initial delivery rate of approximately 4-5 g/minute at an atomizing air pressure of about 200 kPa (2 bar). After delivery of about 30% of the spraying dispersion, the delivery rate is increased to 9-11 g/minute.

When the spraying process is completed, the coated spheres are dried with 40-60° C. dry inlet air for about 10 minutes. The coated spheres are then allowed to cool in the fluid bed with inlet air temperature of 20-25° C. for about 5-10 minutes. The dried drug coated spheres are sized using a mesh sieve, and spheres passing through the sieve are discarded.

The spheres retained on the sieve are introduced into the fluidized-bed granulator equipped with the Wurster insert and warmed with 50-60° C. dry inlet air. A previously prepared functional coating dispersion (in a suitable quantity of water) is sprayed onto the fluidized spheres at a delivery rate of about 400 to 500 g/minute with atomizing air pressure of about 250 kPa (2.5 bar). When the spraying process is completed, the spheres are dried using 50-55° C. dry inlet air for about 10 minutes. The coated spheres are allowed to cool in the fluid bed using 20-25° C. dry inlet air, for about 5-10 minutes.

The seal-coated particles are blended with the "Final Blending" ingredients and filled into hard gelatin capsules.

EXAMPLE 16

Metaxalone capsules prepared according to Example 10B were used for a drug dissolution study, comparing with the currently marketed SKELAXIN® 800 mg metaxalone tablet product. Four 200 mg metaxalone capsules and a single SKELAXIN 800 mg tablet are subjected to dissolution in 500 mL of pH 6.8, 50 mM phosphate buffer, using USP type 2 dissolution apparatus (paddle method) with 50 RPM paddle rotation. Results are in the table 14 below, where the values in parentheses are the relative standard deviation percentages from three repetitions.

TABLE 14

| Minutes | Mean Cumulative Percentage of Drug Dissolved | |
| --- | --- | --- |
| | Example 10B | SKELAXIN |
| 5 | 19 (0.2) | 1 (12.2) |
| 10 | 19 (3.3) | 3 (21.3) |
| 15 | 22 (11.8) | 5 (16.4) |
| 30 | 20 (8.9) | 11 (39.0) |
| 45 | 21 (6.6) | 12 (13.7) |
| 60 | 21 (9.2) | 15 (11.1) |
| 120 | 23 (4.5) | 15 (2.6) |

Metaxaone capsules of the example show an enhanced dissolution rate and supersaturation of the drug, compared to the marketed product.

The invention claimed is:

1. A stabilized suspension suitable for oral administration and downstream processing of solid dosage forms, consisting of:
   a) an aqueous solution consisting of an aqueous solvent, a water-soluble surfactant, a de-agglomeration agent and a water-soluble polymer; and
   b) particles of a poorly soluble pharmaceutically active ingredient suspended in the aqueous solution,
   wherein the water-soluble surfactant is an anionic surfactant selected from the group consisting of sodium lauryl sulfate, sodium laureth sulfate, docusate salt, sodium stearate, and a combination thereof, the de-agglomeration agent is an anionic polymer that is a copolymer of methacrylic acid and ethyl acrylate, and the water-soluble polymer is hydroxypropyl methylcellulose,
   wherein the poorly soluble pharmaceutically active ingredient has an average particle size of about 800 nm or less,
   wherein, apart from the water-soluble surfactant and the water-soluble polymer, no other polymer is added to the aqueous solution containing the particles of the poorly soluble pharmaceutically active ingredient before particle size reduction, and
   wherein the stabilized suspension provides a supersaturated concentration of the poorly soluble pharmaceutically active ingredient.

2. The stabilized suspension of claim 1, wherein the ratio of the poorly soluble pharmaceutically active ingredient to the de-agglomeration agent is between 20:1 and 1:20.

3. The stabilized suspension of claim 1, wherein the ratio of the poorly soluble pharmaceutically active ingredient to the de-agglomeration agent is between 5:1 and 1:5.

4. The stabilized suspension of claim 1, wherein the ratio of the poorly soluble pharmaceutically active ingredient to the de-agglomeration agent is between 3:1 and 1:3.

5. The stabilized suspension of claim 1, wherein the particles of the poorly soluble pharmaceutically active ingredient have an average size of about 500 nm or less.

6. The stabilized suspension of claim 1, wherein the anionic surfactant is selected from the group consisting of docusate salt and sodium lauryl sulfate.

7. A method of treating a patient comprising administering the stabilized suspension of claim 1.

8. A dry powder consisting of:
   a) a water-soluble surfactant, a de-agglomeration agent, and a water-soluble polymer; and
   b) particles of a poorly soluble pharmaceutically active ingredient, wherein the water-soluble surfactant is an anionic surfactant selected from the group consisting of sodium lauryl sulfate, sodium laureth sulfate, docusate salt, sodium stearate, and a combination thereof, the de-agglomeration agent is an anionic polymer that is a copolymer of methacrylic acid and ethyl acrylate, and the water-soluble polymer is hydroxypropyl methylcellulose,
   wherein the poorly soluble pharmaceutically active ingredient has an average particle size of about 800 nm or less, and
   wherein, apart from the water-soluble surfactant and the water-soluble polymer, no other polymer is present before particle size reduction.

9. The dry powder of claim 8, wherein the dry powder is loaded into a capsule.

* * * * *